US012646612B2

(12) United States Patent
Kadrolkar et al.

(10) Patent No.: US 12,646,612 B2
(45) Date of Patent: *Jun. 2, 2026

(54) EARLY WARNING OF LVAD THROMBUS FORMATION

(71) Applicant: Boston Scientific Scimed, Inc., Maple Grove, MN (US)

(72) Inventors: Abhijit Kadrolkar, Minneapolis, MN (US); Robert W. Stadler, Shoreview, MN (US); Michael C. Brown, Dresher, PA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/502,117

(22) Filed: Oct. 15, 2021

(65) Prior Publication Data

US 2022/0032035 A1    Feb. 3, 2022

Related U.S. Application Data

(63) Continuation of application No. 16/248,888, filed on Jan. 16, 2019, now Pat. No. 11,154,702.

(Continued)

(51) Int. Cl.
*A61M 60/50* (2021.01)
*A61M 60/148* (2021.01)
(Continued)

(52) U.S. Cl.
CPC .......... *G16H 40/63* (2018.01); *A61M 60/148* (2021.01); *A61M 60/178* (2021.01);
(Continued)

(58) Field of Classification Search
CPC .......................... A61M 2205/18; A61M 1/122
See application file for complete search history.

(56) References Cited

U.S. PATENT DOCUMENTS

| 7,997,854 B2 | 8/2011 | LaRose et al. |
| 8,007,254 B2 | 8/2011 | LaRose et al. |

(Continued)

FOREIGN PATENT DOCUMENTS

| CN | 101678160 A | 3/2010 |
| WO | 2015183922 A1 | 12/2015 |
| WO | 2017079111 A1 | 5/2017 |

OTHER PUBLICATIONS

Samer S. Najjar, MD, et al., An analysis of pump thrombus events in patients in the HeartWare ADVANCE bridge to transplant and continued access protocol trial, The Journal of Heart and Lung Transplantation, Elsevier Inc., http://dx.doi.org/10.1016/j.healun.2013.12.001, 12 pages.

(Continued)

*Primary Examiner* — Jennifer Pitrak McDonald
*Assistant Examiner* — Jennifer L Ghand
(74) *Attorney, Agent, or Firm* — Seager Tufte & Wickhem, LLP

(57) ABSTRACT

A method of determining an adverse event within a patient having an implantable blood pump including calculating a plurality of power consumption trends of the blood pump during a plurality of time periods using a low-pass filter, determining a plurality of power trend differences between the plurality of power consumption trends, calculating a total amount of the plurality of power trend differences during a time interval, and generating an alarm when the total amount of the plurality of power trend differences exceeds a pre-determined threshold.

18 Claims, 9 Drawing Sheets

Related U.S. Application Data

(60) Provisional application No. 62/622,488, filed on Jan. 26, 2018.

(51) Int. Cl.

| | |
|---|---|
| *A61M 60/178* | (2021.01) |
| *A61M 60/216* | (2021.01) |
| *A61M 60/422* | (2021.01) |
| *A61M 60/508* | (2021.01) |
| *A61M 60/585* | (2021.01) |
| *G16H 40/63* | (2018.01) |

(52) U.S. Cl.
CPC ........ *A61M 60/216* (2021.01); *A61M 60/422* (2021.01); *A61M 60/508* (2021.01); *A61M 60/585* (2021.01); *A61M 2205/18* (2013.01); *A61M 2205/3327* (2013.01); *A61M 2205/50* (2013.01)

(56) References Cited

U.S. PATENT DOCUMENTS

| | | | |
|---|---|---|---|
| 8,419,609 | B2 | 4/2013 | Shambaugh, Jr. et al. |
| 8,512,013 | B2 | 8/2013 | LaRose et al. |
| 9,511,179 | B2 | 12/2016 | Casas et al. |
| 9,561,313 | B2 | 2/2017 | Taskin |
| 9,974,894 | B2 | 5/2018 | Morello |
| 11,154,702 | B2 * | 10/2021 | Kadrolkar ........... A61M 60/585 |
| 2001/0021817 | A1 * | 9/2001 | Brugger .............. A61M 60/546 604/6.11 |
| 2003/0199727 | A1 | 10/2003 | Burke et al. |
| 2008/0242943 | A1 | 10/2008 | Cuddihy et al. |
| 2012/0142998 | A1 | 6/2012 | Ogawa et al. |
| 2014/0268213 | A1 | 9/2014 | Ebner et al. |
| 2017/0119256 | A1 | 5/2017 | Demou et al. |
| 2018/0085507 | A1 | 3/2018 | Casas et al. |
| 2019/0015040 | A1 | 1/2019 | Voskoboynikov et al. |
| 2022/0032035 | A1 * | 2/2022 | Kadrolkar ........... A61M 60/422 |

OTHER PUBLICATIONS

Katherine Chorpenning, et al., HeartWare Controller Logs A Diagnostic Tool and Clinical Management Aid for the HVAD Pump, ASAIO Journal 2013, DOI: 10.1097/MAT.0000000000000022, 4 pages.

International Search Report and Written Opinion dated May 2, 2019, for corresponding International Application No. PCT/US2019/013731; International Filing Date: Jan. 16, 2019 consisting of 11 pages.

First Office Action and Search Report, and translation thereof, from counterpart Chinese Application No. 201980010114.5 dated Jan. 11, 2023, 16 pp.

* cited by examiner

EARLY WARNING OF LVAD THROMBUS FORMATION

CROSS-REFERENCE TO RELATED APPLICATION

This application is a continuation of U.S. application Ser. No. 16/248,888, filed Jan. 16, 2019, and claims the benefit of U.S. Application Ser. No. 62/622,488, filed Jan. 26, 2018, which is hereby incorporate herein in the entirety.

FIELD

The present technology is generally related to blood pumps and determining an adverse event associated therewith.

BACKGROUND

Mechanical Circulatory Support Devices ("MCSDs") are lifesaving mechanical devices configured to assist the heart in pumping blood throughout the body. A known type of MCSD is a ventricular assist device ("VAD") which may include a centrifugal pump, axial pump, or another type of electromagnetic pump configured to pump blood from the heart to the rest of the body. One such centrifugal pump is the HVAD® Pump and one such axial pump is the MVAD® Pump, each manufactured by HeartWare, Inc. in Miami Lakes, Fla., USA.

VADs are desirably provided with a rotor and contactless bearings so that, in operation, the rotor floats within the housing. With contactless bearings, there is no solid-to-solid contact between the rotor and the housing, and thus no mechanical wear during operation. One form of contactless bearing is a hydrodynamic bearing. In a hydrodynamic bearing, the liquid being pumped passes between a surface of the rotor and the surfaces of a hydrodynamic bearing which creates a clearance that is many times larger than the dimensions of blood cells. The surfaces are configured so that as the rotor turns, the fluid disposed between these surfaces exerts pressure on the surface of the rotor that holds the rotor away from the housing. However, in some cases the blood passing through the blood pump may contain particles of thrombus, a solid or semi-solid deposit generated within a patient's body. Such thrombus may lead to pump failure, necessitate pump replacement, and/or be accompanied by patient morbidity or mortality.

Determining adverse events, such as the above-mentioned thrombus, gastrointestinal bleeding, tachycardia, arrhythmia, right heart failure, and the like, in patients having an implanted VAD is challenging as such patients have different cardiac pathologies that necessitated the VAD implantation. One solution devised to detect adverse events, is to implant sensors into or onto the VAD to detect operating parameters of the blood pump. Implanting such sensors, however, requires sensor calibration, which is subject to failure from corrosion or other events. Further, such sensors and the corresponding calibration increases the power necessary to operate the VAD. Other solutions include detection methods that lack sensitivity and which are prone to triggering false alarms.

SUMMARY

The techniques of this disclosure generally relate to blood pumps and determining an adverse event associated therewith.

In one aspect, the present disclosure provides a method of determining an adverse event within a patient having an implantable blood pump, the method including calculating one or more power consumption trends of the blood pump during a time periods using a first low-pass filter and a second low-pass filter; determining one or more power trend differences between the power consumption trends; calculating a total amount of the power trend differences during a time interval; and generating an alarm when the total amount of the power trend differences exceeds a pre-determined threshold.

In another aspect, calculating the power consumption trends includes calculating a short-term trend using the first low-pass filter.

In another aspect, calculating the power consumption trends includes calculating a long-term trend using the second low-pass filter, the second low-pass filter having a cutoff frequency lower than a cutoff frequency of the first low-pass filter.

In another aspect, the disclosure provides the cutoff frequency of the first low-pass filter being a first optimized constant between 50 to 150 microHertz and the cutoff frequency of the second low-pass filter is a second optimized constant between 0.5 to 1.0 microHertz.

In another aspect, the disclosure provides calculating the pre-determined threshold using a percentage of at least one of the power consumption trends.

In another aspect, the disclosure provides the first low-pass filter being a moving average filter defining a first moving average and a second moving average longer than the first moving average, the first moving average being between 1 to 20 hours and the second moving average being between 1 to 20 days.

In another aspect, the disclosure provides calculating the total amount of the plurality of power trend differences during the time interval using an integrator, the time interval being between 5 to 25 hours.

In another aspect, the disclosure provides calculating the total amount of the power trend differences during the time interval using an integrator, the time interval being a 24-hour time interval.

In another aspect, the disclosure provides calculating a high-power threshold using at least one of the power consumption trends; calculating a real-time power value of the blood pump; and generating an alarm when the real-time power value exceeds the high-power threshold.

In one aspect, the present disclosure provides a method of determining an adverse event from power consumption of an implantable blood pump, the method including calculating one or more differences in power consumption of the blood pump over one or more time periods using one or more low-pass filters; determining an accumulated difference between the differences during a time interval using an integrator; and generating an alarm when the accumulated difference exceeds a primary threshold.

In another aspect, calculating the differences in power consumption of the blood pump includes calculating at least one of a group consisting of a current, a voltage, a back electromotive force, and a plurality of power consumption trends.

In another aspect, the disclosure provides the low-pass filters including a first low-pass filter and a second low-pass filter, and the first low-pass filter and the second low-pass filter including one of the group consisting of a cutoff frequency and a time constant.

In another aspect, the disclosure provides determining the accumulated difference during a 24-hour time interval using the integrator.

In another aspect, the disclosure provides normalizing the accumulated difference by dividing by at least one of the differences in power consumption of the blood pump over the time periods.

In another aspect, the disclosure provides calculating a high-power threshold using a power consumption trend; determining a real-time power value of the blood pump; and generating an alarm when the real-time power value exceeds the high-power threshold.

In another aspect, the disclosure provides the power consumption trend including a long-term trend.

In one aspect, the present disclosure provides a method of determining an adverse event within a patient having an implantable blood pump, the method including determining an expected pump power for a select speed of the blood pump; determining a speed-dependent threshold using the determined expected pump power; determining a real-time pump power relative to the select speed; comparing the speed-dependent threshold to the real-time pump power; and generating an alarm when the real-time pump power exceeds the speed-dependent threshold.

In another aspect, the disclosure provides multiplying the expected pump power by a percentage to obtain the speed-dependent threshold.

In another aspect, the expected pump power is multiplied by a percentage between 120% to 160%.

In another aspect, the speed-dependent threshold includes an upper limit and a lower limit relative to the expected pump power.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
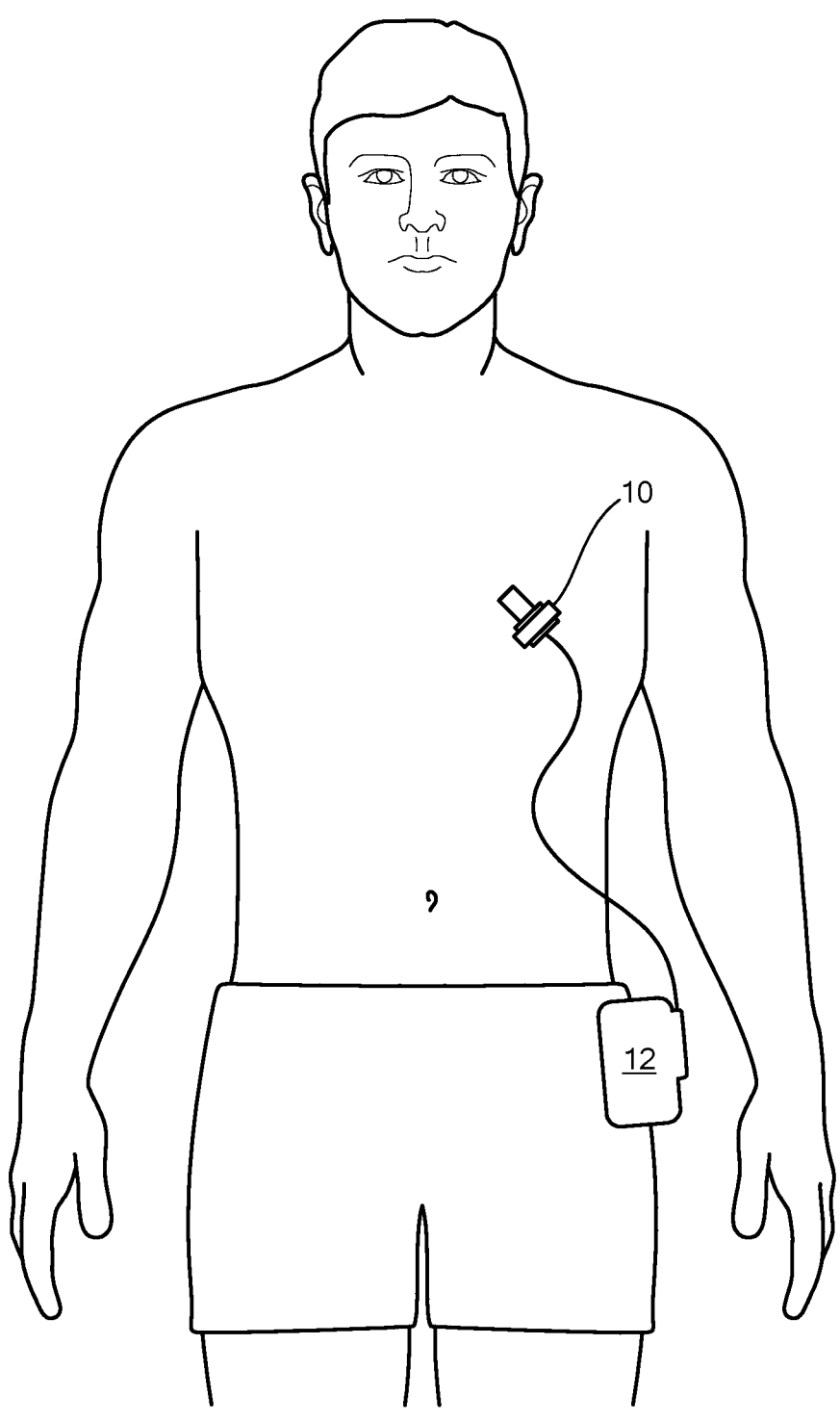
FIG. 1 is a diagram of an exemplary blood pump implanted within a patient and a controller configured to be in communication with the blood pump.

Before describing in detail exemplary embodiments, it is noted that the embodiments reside primarily in combinations of apparatus components and processing steps related to determining an adverse event within a patient having an implantable blood pump. Accordingly, the system and method components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

As used herein, relational terms, such as "first" and "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

In embodiments described herein, the joining term, "in communication with" and the like, may be used to indicate electrical or data communication, which may be accomplished by physical contact, induction, electromagnetic radiation, radio signaling, infrared signaling or optical signaling, for example. One having ordinary skill in the art will appreciate that multiple components may interoperate and modifications and variations are possible of achieving the electrical and data communication.

Referring now to the drawings in which like reference designators refer to like elements there is shown in FIG. 1 an exemplary implantable blood pump 10 configured to be implanted within a patient, such as a human or animal patient. The blood pump 10 may be, without limitation, the HVAD® Pump or the MVAD® Pump, having a movable element, such as a rotor, configured to pump blood from the heart to the rest of the body. The HVAD® Pump is further discussed in U.S. Pat. Nos. 7,997,854 and 8,512,013, the disclosures of which are incorporated herein by reference in the entirety. The MVAD® Pump is further discussed in U.S.
Pat. Nos. 8,007,254, 8,419,609, and 9,561,313, the disclo-
sures of which are incorporated herein by reference in the
entirety. The blood pump 10 may be fully or partially
implanted within the patient and may be in communication
with a controller 12 or performing one or more of the
method steps disclosed herein. The controller 12 may be
positioned external to the patient or may be implanted within
the patient.

Figure 2:
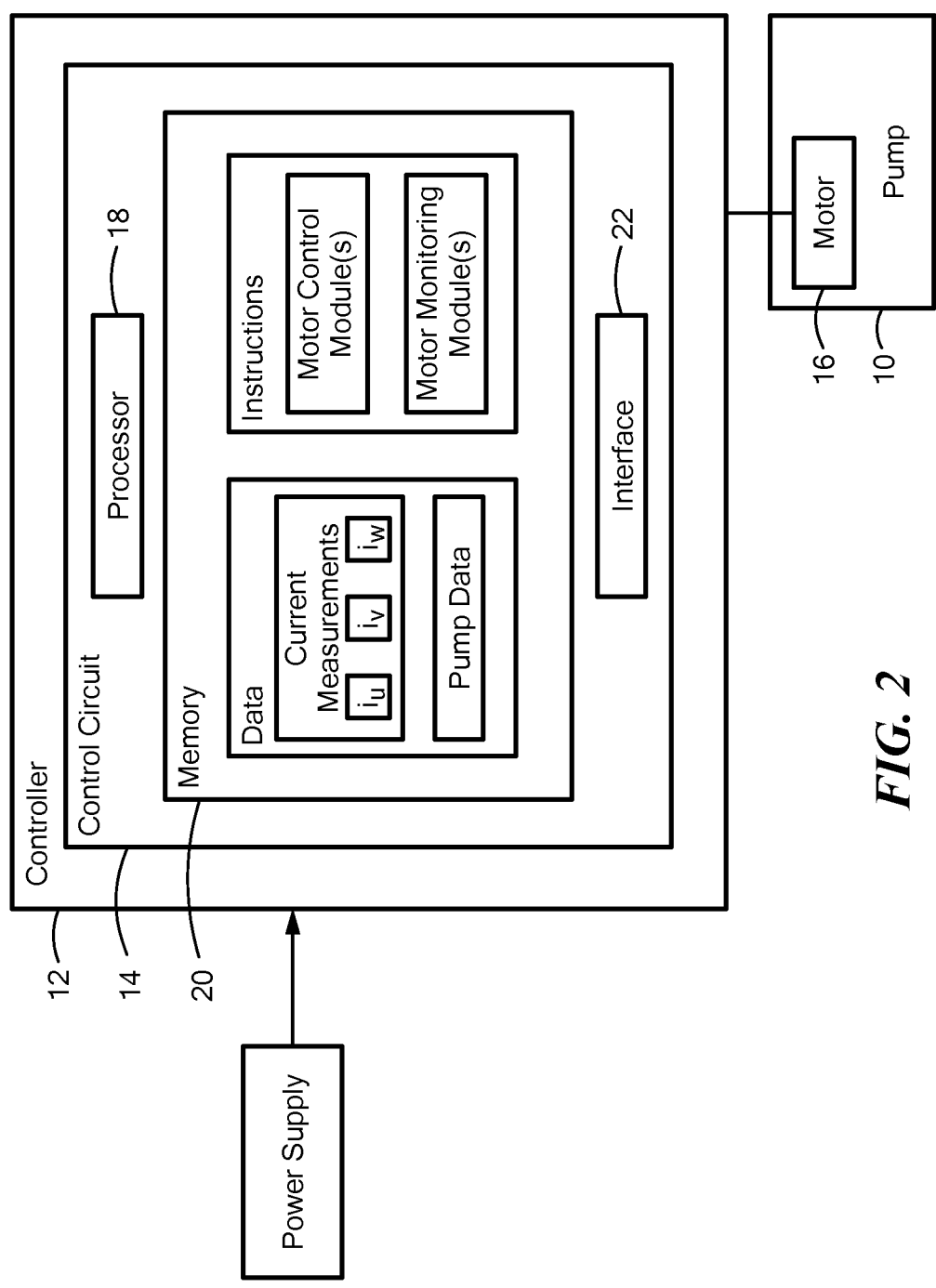
FIG. 2 is a block diagram of the exemplary implantable blood pump and the controller of FIG. 1.

FIG. 2 is a block diagram of an exemplary system
including the blood pump 10 and the controller 12. The
controller 12 is configured to determine an adverse event
associated with the patient having the implanted blood pump
10 by determining an expected or average pump power
usage and an unexpected increase in the pump power usage
relative thereto. The unexpected increase in power triggers
an alarm. One such adverse event may be the presence of
thrombus inside of the blood pump 10, which is known to
increase the power needed to maintain the blood pump 10 at
a desired speed relative to the average speed. Other adverse
events associated with operation of the blood pump 10
include, but are not limited to, ingestion, GI bleed, occlu-
sion, or the like. In addition to or in lieu of tracking the blood
pump's power usage, the blood pump 10 and/or the con-
troller 12 may also determine, monitor, and/or track the
blood pump's electrical current, voltage, and/or back elec-
tromotive force ("EMF"), singularly or in combination, in
order to determine the onset or presence of the adverse
event. Further details associated with methods of determin-
ing current, voltage, EMF, and the like, within a blood pump
are disclosed in commonly owned U.S. Pat. No. 9,511,179,
which is hereby incorporated by reference in the entirety.

The controller 12 includes a control circuit 14 having
control circuitry configured to monitor and control startup
and subsequent operation of a motor 16 implanted within the
blood pump 10. The controller 12 may also include a
processor 18 having processing circuitry, a memory 20, and
an interface 22. The memory 20 may be configured to store
information accessible by the processor 18, including
instructions executable by the processor 18 and/or data that
may be retrieved, manipulated or stored by the processor 18.
Further details associated with an exemplary controller 12
are disclosed in commonly owned U.S. patent application
Ser. No. 15/710,323, which is hereby incorporated by ref-
erence in the entirety.

Figure 3:
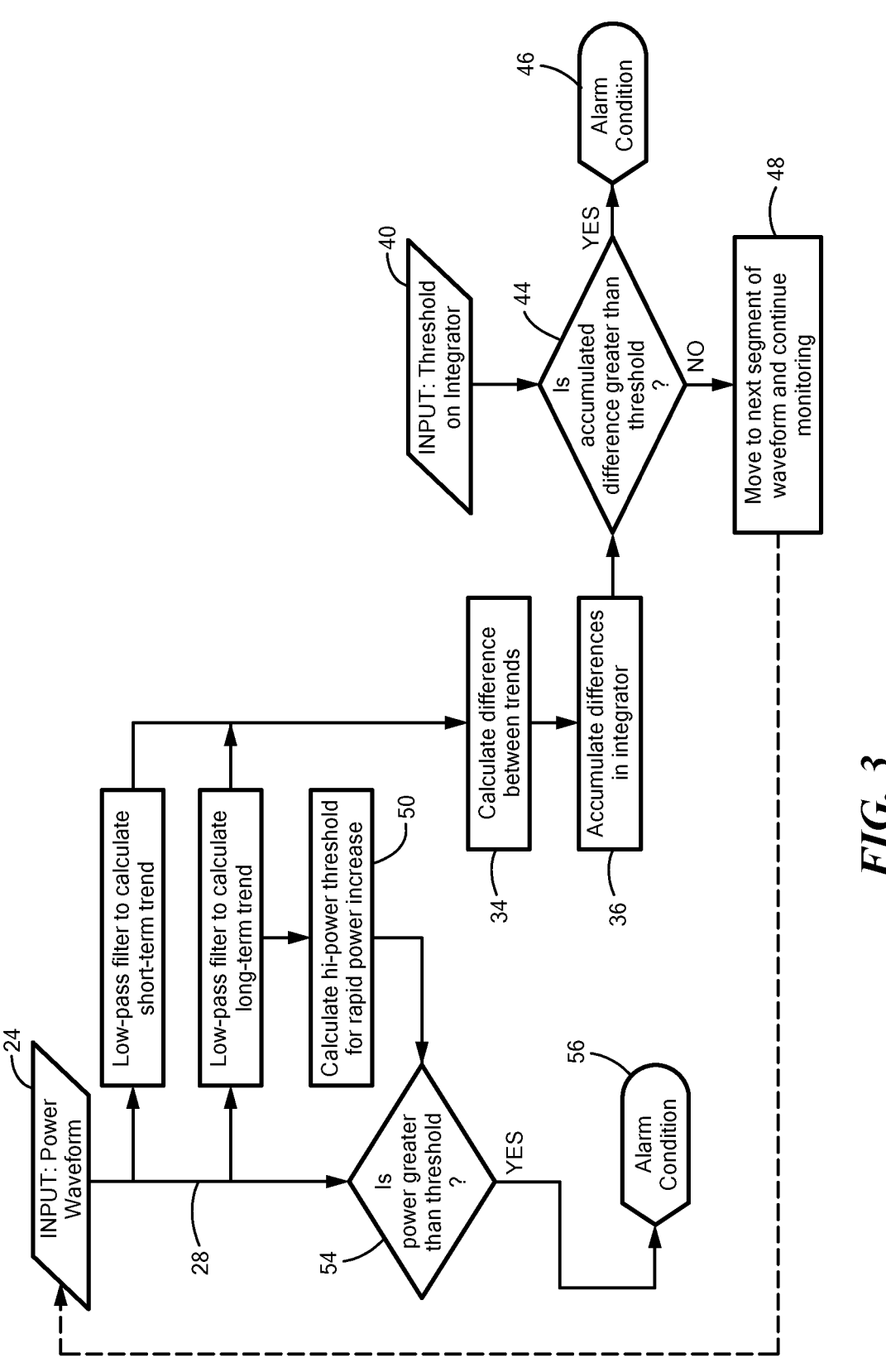
FIG. 3 is an exemplary flow chart showing a method of determining an adverse event within a patient having the implantable blood pump implanted within the patient.
Figure 4:
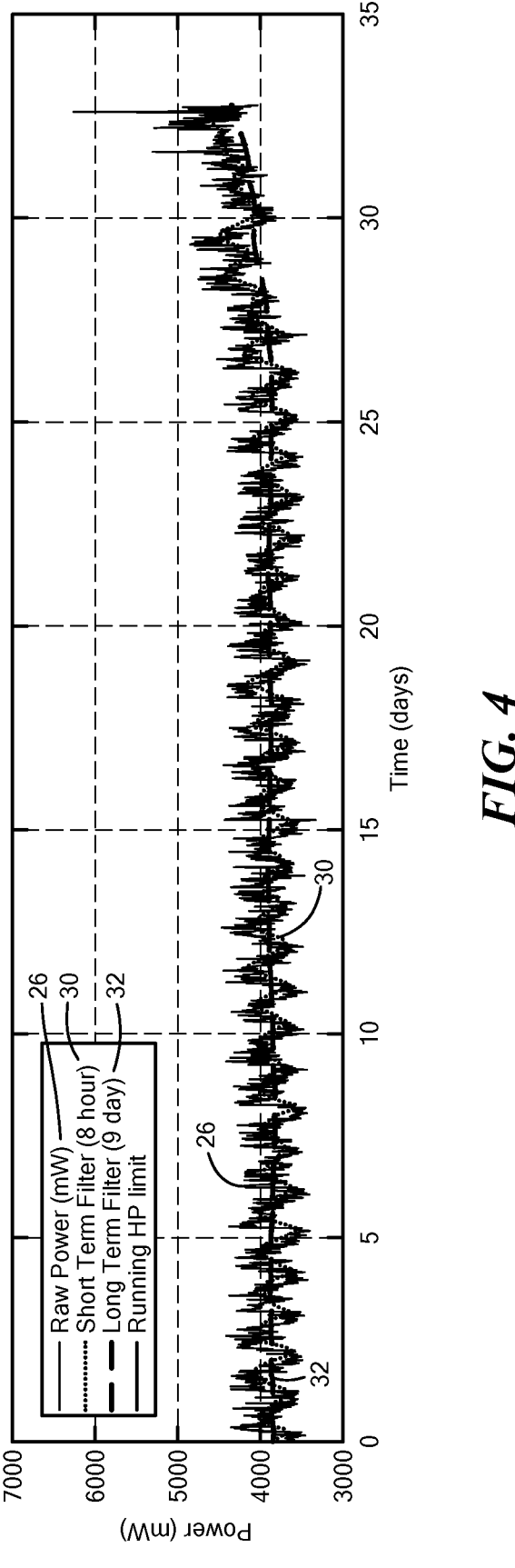
FIG. 4 is an exemplary graph depicting power consumption of the implantable blood pump of FIG. 1 over time.

FIG. 3 is a flow chart that illustrates method steps which
may be used by the system to perform the method disclosed
herein. One or more steps may be added and/or omitted and
the order of the steps may differ from that which is shown.
In one configuration, the method begins with step 24 includ-
ing the controller 12 detecting the amount of power used by
the blood pump 10. FIG. 4 is an exemplary graph that
illustrates a power waveform 26 showing the amount of
power detected. In step 28, the method continues with the
controller 12 calculating one or more power consumption
trends ("trends") of the blood pump 10 during at least
one-time period using one or more low-pass filters. The
trends provide the expected or average pump power usage
and detect relatively slowly evolving increases in pump
power usage relative thereto as an indication of the adverse
event.

The step of calculating the trends may include calculating
a short-term trend using a first low-pass filter and calculating
a long-term trend using a second low-pass filter. The first
low-pass filter and the second low-pass filter eliminate
frequencies above one or more cutoff frequencies, while
passing the frequencies below the cutoff frequencies unchanged. In the alternative, the first and second low-pass
filters may be moving average filters. In other configura-
tions, such as when comparing a relatively smooth power
trend to an expected pump power, a single low-pass filter
may be used, the output of which may be compared to the
expected power.

When utilizing the first and second low-pass filters having
the cutoff frequencies, the second low-pass filter may
include a cutoff frequency lower than a cutoff frequency of
the first low-pass filter. For example, the cutoff frequency of
the first lowpass filter may be a first optimized constant or
time constant between 50 to 150 microhertz, such as 92.6
microhertz, and the cutoff frequency of the second lowpass
filter may be a second optimized constant between 0.5 to 1.0
microhertz, such as 0.77 microhertz.

With reference to FIG. 4, when the first and the second
low-pass filters are moving average filters, the first-low pass
filter may define a first moving average filter (first filter
interval) between 1 to 20 hours, such as 8 hours. The output
of the first low-pass filter is generally designated as "30."
The second low-pass filter may define a second moving
average filter (second filter interval) longer than the first
moving average filter, for example, between 1 to 20 days,
such as 9 days. The output of the second-low pass filter is
generally designated as "32."

In step 34, the controller 12 may determine or calculate
numerous differences between the power trends. In other
configurations, the differences may include differences in
power trends, electrical current, voltage, back EMF, or a
combination thereof. The differences may be calculated
using outputs from the first and second low-pass filters
which may be in the form of the cutoff frequencies or the
moving averages.

Figure 5:
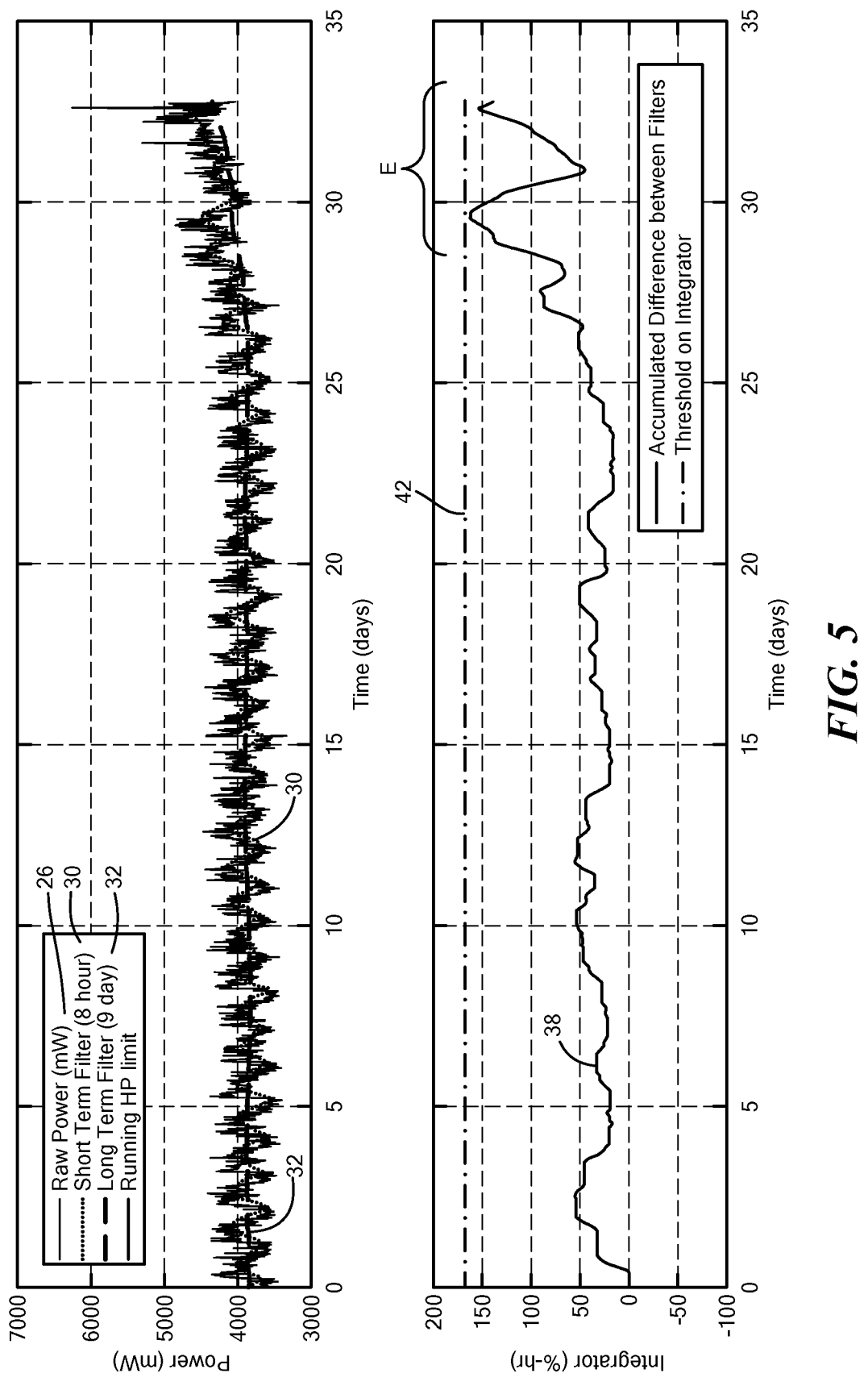
FIG. 5 is the exemplary graph of FIG. 4 and an exemplary graph depicting an accumulated difference in power consumption over time relative to a pre-determined threshold.
Figure 6:
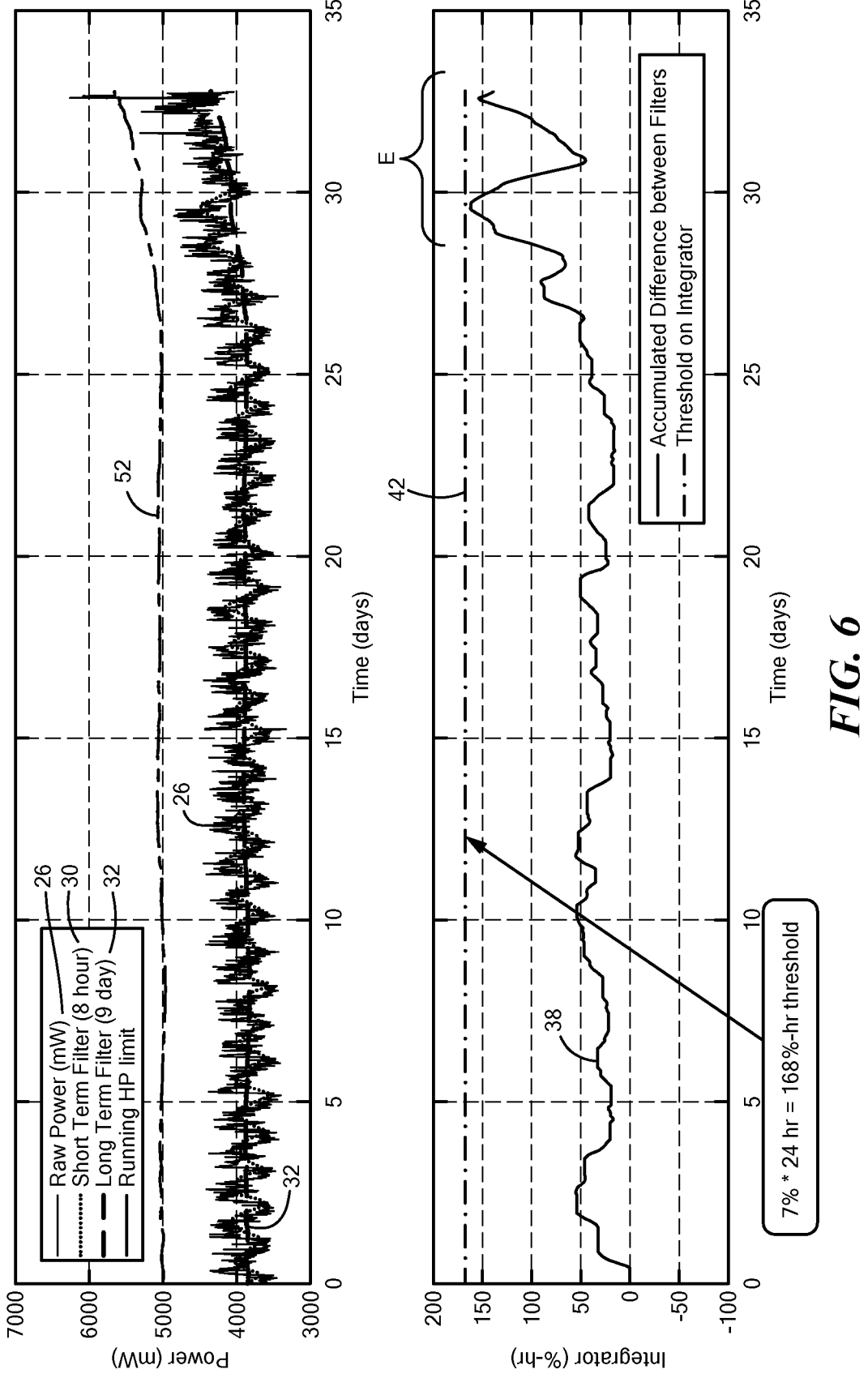
FIG. 6 is the exemplary graph of FIG. 5 depicting a high-power threshold and the exemplary graph of FIG. 4.

In step 36, the calculated differences may be accumulated
over a time interval using an integrator. For example, FIGS.
5 and 6 depict an accumulated difference waveform 38
showing the accumulated differences between the output of
the first low-pass filter 30 and the output of the second
low-pass filter 32 as a function of the integrator relative to
time. The time interval may vary as a finite or infinite
window and may be between 5 to 25 hours, such as a
24-hour time interval, in attempt to avoid circadian varia-
tion. In other words, an indication of change in pump power
usage over a 24-hour time period may be determined by
calculating the pump power usage differences between the
trends and accumulating the differences in the integrator.
The accumulated difference is normalized by the output of
the second low-pass filter 32, thus converting the accumu-
lated difference to a percentage deviation from a long-term
power trend, the long-term trend being the output of the
second low-pass filter 32.

When attempting to detect thrombus or ingestion, the
method constrains the accumulated difference waveform 38
to an amount greater than or equal to zero. In addition to
detecting the thrombus or ingestion, such as when attempt-
ing to detect GI bleed or occlusion, the method may include
constraining the accumulated difference waveform 38 to an
amount less than or equal to zero.

In step 40, a pre-determined threshold 42 or primary
threshold is applied to the accumulated difference between
the outputs of the first and second low-pass filters. The
pre-determined threshold is normalized to a percentage of
the second low-pass filter. In other words, the primary
threshold is a threshold percentage multiplied by the time
interval. For example, with reference to the graphs of FIG.
6, a threshold percentage between 6% to 10%, such as 7%,
is multiplied by the 24-hour time interval to obtain a pre-determined threshold of 168%. Such amounts are provided as exemplary only and may vary between patients and pump parameters.

In step 44, the controller 12 is configured to determine whether the accumulated difference exceeds the pre-determined threshold 42 and if exceeded, in step 46, the blood pump 10 and/or the controller 12 generates an alarm indicative of a potential or existing adverse event. For example, FIGS. 5 and 6 depict the accumulated difference waveform 38 exceeding the pre-determined threshold 42 at a region generally designated as "E." The alarm may be audible, visual, vibratory, or the like, and may be sent wirelessly to from the controller 12 to a remote location, such as a physician's office. In one example, the alarm may be sent to the physician's office in a manner that is silent or otherwise not detectable by the patient. The controller 12 may be manually or systematically reset, such as when a physician determines that a manual reset of the short and long-term trends may be desirable. If the pre-determined threshold 42 is not exceeded, in step 48, the controller 12 continues to monitor the power usage of the blood pump 10.

With reference again to the flow chart of FIG. 3 and the graphs of FIG. 6, once the short-term and long-term trends are determined, the controller 12 may be configured to detect relatively quickly evolving adverse events. For example, in step 50, the method includes the controller 12 calculating a high-power threshold 52 or a secondary threshold (FIG. 6) using at least one of the power consumption trends, such as information obtained from the long-term trend. In step 54, the controller 12 determines the real-time power value of the blood pump 10, depicted using the power waveform 26, and compare the real-time power value to the high-power threshold 52. In step 56, the controller 12 generates an alarm when the real-time power value exceeds the high-power threshold 52. The real-time power value that is compared to the high-power threshold 52 may be the power averaged over a relatively short duration, such as 15 minutes. The alarm generated with respect to the relatively quick or rapid power increase may include the same or similar features as the alarm generated with respect to the relatively slowly evolving power increase. In other configurations, the alarm may differ, such as to signify a higher risk or emergency situation.

In one configuration, the controller 12 may be programmed to automatically initialize and perform the disclosed method after implantation of the blood pump 10. For example, the method may be activated between 20 to 22 days following the implantation when the patient has healed from the implantation surgery. In another configuration, the controller 12 may be configured to automatically begin to track power usage once a period of patient stability is detected, for example, when the pump power usage indicates stable levels for a predetermined time period. In one configuration, the initialization of the method may include averaging the pump power usage over a 24-hour period and setting the initial value of the first and second low-pass filter outputs to the average pump power usage of the 24-hour period. The 24-hour period may be used in an attempt to avoid circadian variation, however other time intervals may be utilized. In another configuration, a select initialization value may be manually input, such as by the physician. The reset process may be implemented in the same or a similar manner as the initialization method.

Figure 7:
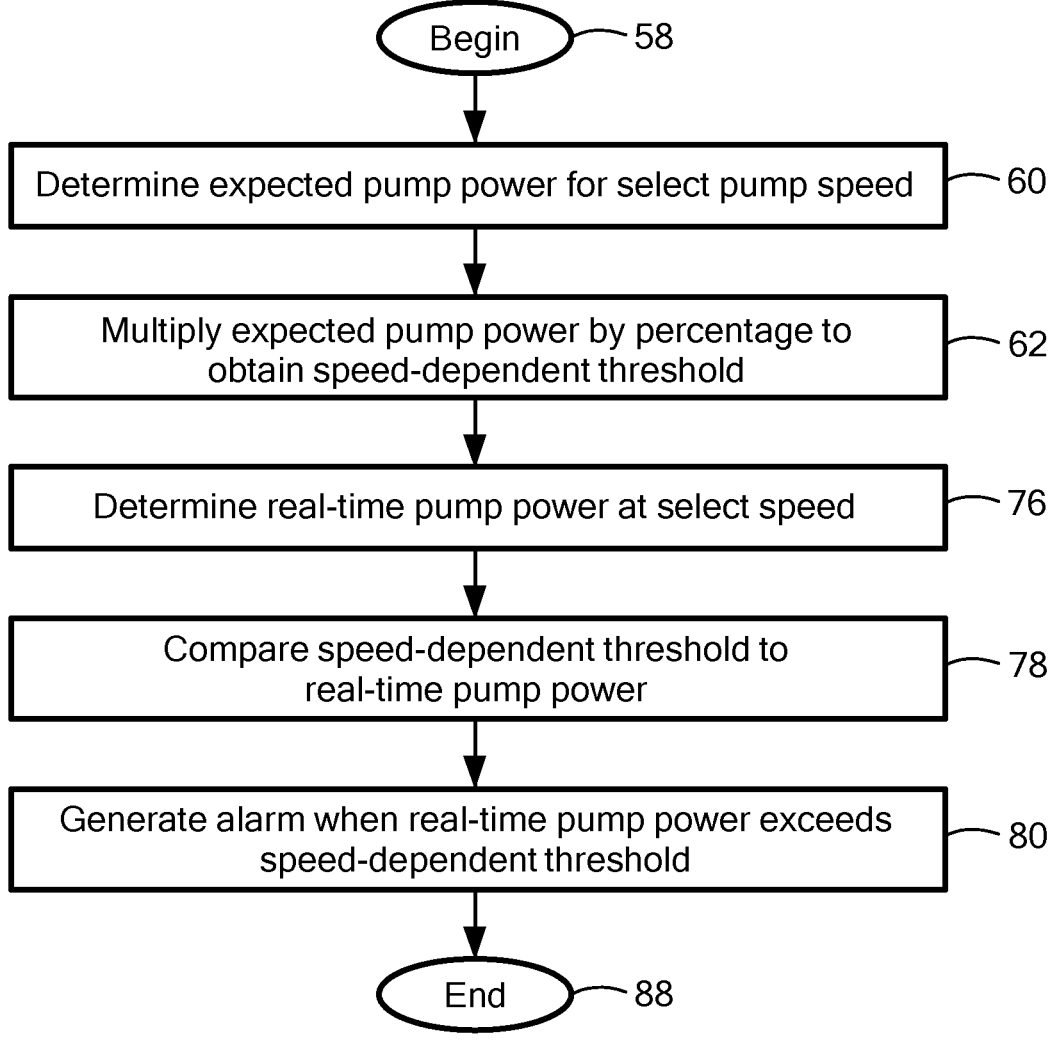
FIG. 7 is an exemplary flow chart showing another configuration of a method of determining an adverse event within a patient having the implantable blood pump implanted within the patient.

Referring now to FIG. 7, another configuration of a method for determining the adverse event within the patient is depicted using a flow chart having numerous method steps. The method steps provided are not intended to be limiting and one or more steps may be added and/or omitted and the order of the steps may differ from that which is shown. The method may include using a speed-dependent threshold independent of the moving average filters. When the speed-dependent threshold is crossed, the alarm may be generated in the manner described above. Such method may assist in preventing relatively slow rises in power over a relatively longer time period.

The method begins at step 58 and proceeds to step 60 including determining an expected pump power or pump power usage of the blood pump 10 for a select speed using one or more blood pump parameters, such as pump speed, power consumption, and/or estimated flow. For example, the expected pump power relative to one or more pump select speeds is determined for the patient using H-Q curves which define a relationship between calculated pump pressure head and an estimated flow for a range of rotational speeds. Such determination may include recording one or more regions of constant pump speed and recording and analyzing changes in the speed amounts, such as in a log file over a duration, such as one to two weeks. The expected pump power analysis accounts for circadian fluctuation in flow during hours in which the patient is active or inactive.

Figure 8:
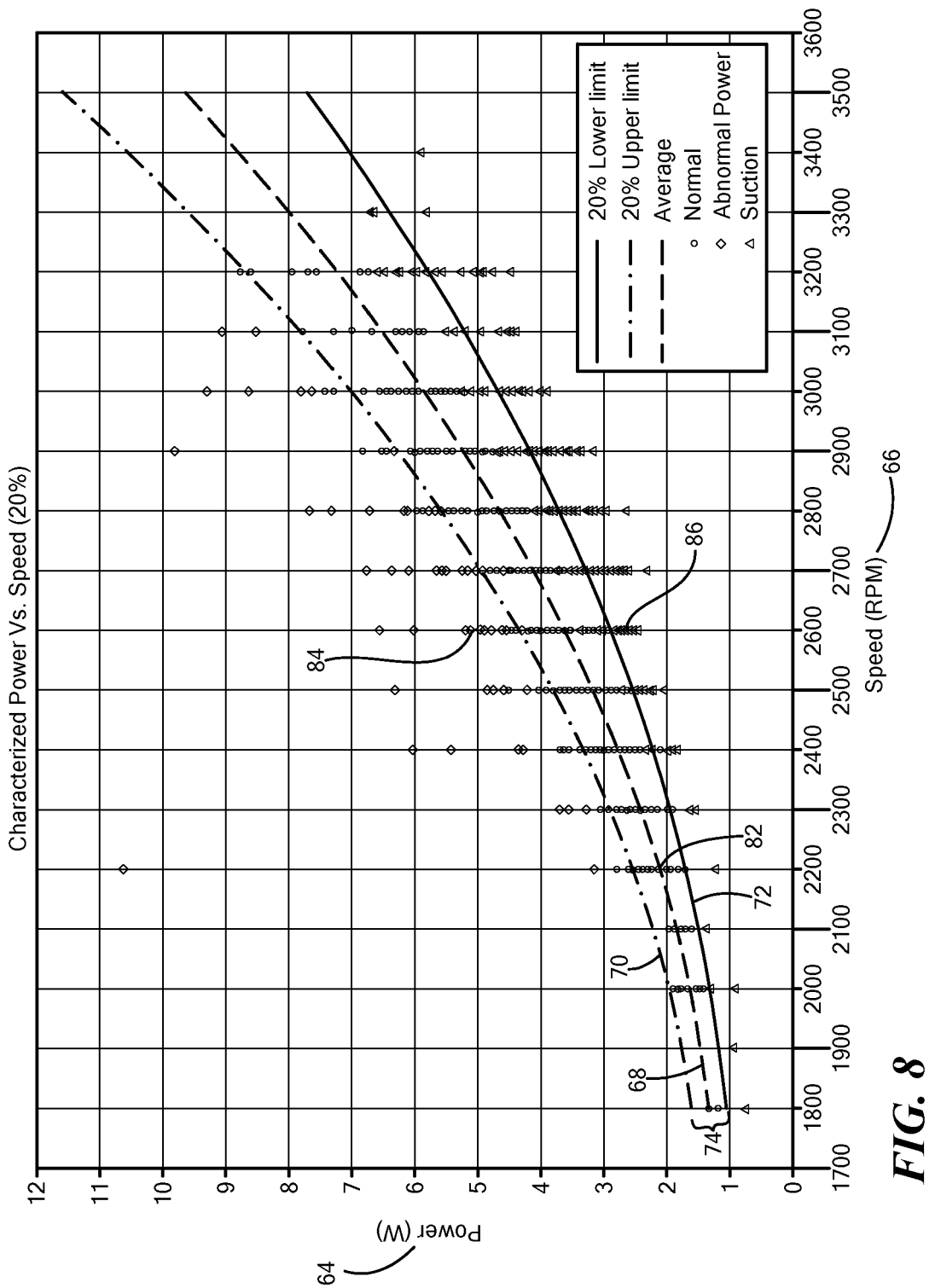
FIG. 8 is an exemplary graph depicting the method of FIG. 7 including determining an expected power consumption of the implantable blood pump at a select speed and a real-time power consumption of the implantable blood pump at the select speed relative to a speed-dependent threshold.

Once the expected pump power for the select speed is determined, the method may include step 62 of multiplying the expected pump power for the select speed by a percentage to obtain a speed-dependent threshold. In other words, the expected pump power is used to determine the speed-dependent threshold. In one example, the percentage is between 120% to 160%, such as 150%, however, other percentages may be used. For example, with reference to FIG. 8, an exemplary graph is shown depicting the pump power, generally designated as "64," relative to the pump speed, generally designated as "66." The expected pump power for each speed is designated generally using the dashed dotted line 68. A 20% band is depicted using solid lines around the expected pump power 64, the band including a 20% upper limit 70 and a 20% lower limit 72, to differentiate the expected pump power 68 from an abnormal power at the select speed. Although a 20% band is shown, other percentages may be used, such as between bands between 10% to 25%. The bands are configured to produce various percentages of accuracy. In one configuration, the speed-dependent threshold 74 is the region between the upper limit 70 and the lower limit 72.

The method continues to step 76 of determining the real-time pump power for the select speed of the blood pump 10 and step 78 of comparing the speed-dependent threshold 74 to the real-time pump power at the select speed. The real-time pump power may be determined using the controller 12 or another method as described above. If the real-time pump power at the select speed exceeds the speed-dependent threshold 74, the method proceeds to step 80 of generating the alarm in the manner described above. If the speed-dependent threshold 74 is not exceeded, the controller 12 may continue to monitor the real-time pump power or may cease monitoring.

The real-time pump power for each rotational speed is designated using a dot symbol, generally designated as "82," when the real-time pump power for the speed is within the speed-dependent threshold 74. An abnormal pump power at the select speed relative to the speed-dependent threshold 74 is shown adjacent to and above the upper limit 70 using a diamond symbol generally designated as "84." A triangle symbol adjacent and below the lower limit 72 and is depicted generally as "86." The triangle symbol and the correspondence location may indicate an adverse event, such as a suction condition. The suction condition may lead to thrombus or another adverse event. Similarly, the abnormal power amount may also indicate one or more adverse events. As such, the method includes generating the alarm upon the detection of the real-time pump power at the select speed being outside of the speed-dependent threshold 74. The method ends at step 88.

Figure 9:
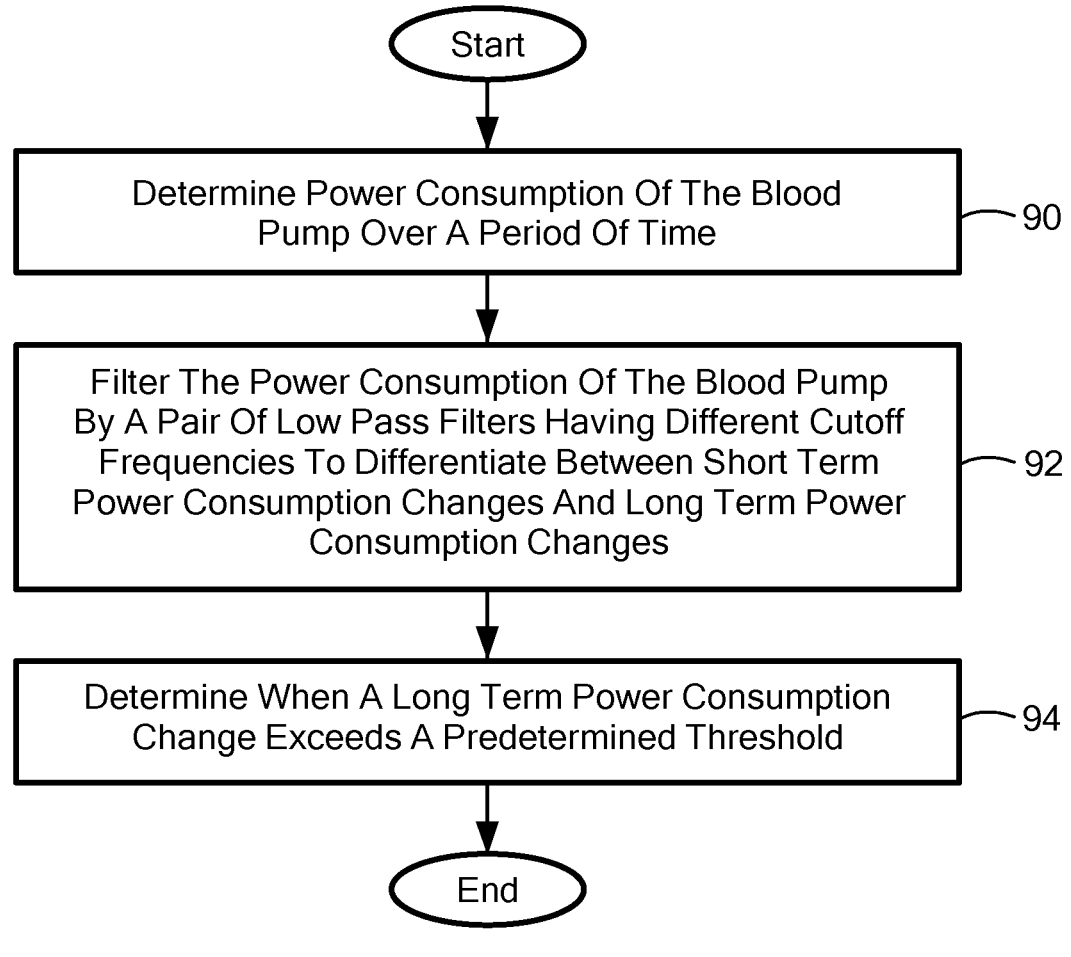
FIG. 9 is a flowchart of a first example process for determining an adverse event in a patient having an implanted blood pump according to principles set forth herein.

FIG. 9 is a flowchart of an example process for determining an adverse event in a patient having an implanted blood pump according to principles set forth herein. The process may be performed by the control circuit 14 of the controller 12. The process includes determining power consumption of the blood pump over a period of time (Block 90). The process also includes filtering the power consumption of the blood pump by a pair of low pass filters having different cutoff frequencies to differentiate between short term power consumption changes and long term power consumption changes (Block 92). The process further includes determining when a long term power consumption change exceeds a predetermined threshold (Block 94).

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A mechanical circulatory support system, the system comprising:

an implantable blood pump device comprising a motor, the implantable blood pump device being configured to cause blood flow in a patient; and a controller device, in communication with the implantable blood pump device, the controller comprising a memory and processing circuitry configured to:

control the implantable blood pump device to operate the motor;

determine a first plurality of power consumption trends of the implantable blood pump device, while the motor is operating, using a first low-pass filter determine a second plurality of power consumption trends of the implantable blood pump device, while the motor is operating, using a second low-pass filter;

determine a plurality of power trend differences, wherein each power trend difference of the plurality of power trend differences comprises a difference between a value of the first plurality of power consumption trends and a corresponding value of the second plurality of power consumption trends, wherein the value of the first plurality of power consumption trends is determined based on a first filter interval and the corresponding value of the second plurality of power consumption trends is determined based on a second filter interval that is greater in duration than the first filter interval;

determine an accumulation value based on an accumulation of the power trend differences during a time interval using an integrator; and generate an alarm in response to the accumulation value exceeding a pre-determined threshold, wherein the alarm indicates an adverse event associated with the implantable blood pump device in the patient, the adverse event including one of a presence of thrombus, an occlusion in the patient, a gastrointestinal bleed in the patient, or an ingestion.

2. The system of claim 1, wherein:

to determine the first plurality of power consumption trends, the processing circuitry is configured to determine a short-term trend using the first low-pass filter; and to determine the second plurality of power consumption trends, the processing circuitry is configured to determine a long-term trend using the second low-pass filter.

3. The system of claim 1, wherein the plurality of power trend differences comprise one or more of differences between a long term current average and a short term current average, differences between a long term voltage average and a short term voltage average, differences between a long term back electromotive force average and a short term back electromotive force average, or differences between a long term power consumption average and a short term power consumption average.

4. The system of claim 1, wherein the first low-pass filter comprises a first moving average filter for determining a first moving average and the second low-pass filter comprises a second moving average filter for determining a second moving average, wherein the second moving average is longer than the first moving average.

5. The system of claim 1, wherein the second low-pass filter has a cutoff frequency lower than a cutoff frequency of the first low-pass filter.

6. The system of claim 1, wherein the processing circuitry is further configured to determine the pre-determined threshold using a percentage of at least one power consumption trend of the second plurality of power consumption trends.

7. The system of claim 1, wherein the processing circuitry is configured to determine the pre-determined threshold as a patient-specific baseline based on the second low-pass filter.

8. The system of claim 1, wherein the processing circuitry is further configured to:

determine an expected power of the implantable blood pump device for a selected speed of the implantable blood pump device;

determine a speed-dependent threshold using the expected power;

determine a real-time pump power for the implantable blood pump device while the motor is operating at the selected speed;

compare the speed-dependent threshold to the real-time pump power; and generate a second alarm in response to the real-time pump power exceeding the speed-dependent threshold.

9. The system of claim 8, wherein the processing circuitry is further configured to multiply the expected power by a percentage to determine the speed-dependent threshold.

10. The system of claim 8, wherein the speed-dependent threshold includes an upper limit and a lower limit relative to the expected power.

11. The system of claim 1, wherein the implantable blood pump device comprises an electromagnetic device.

12. The system of claim 1, wherein the implantable blood pump device comprises an implantable ventricular assist device.

13. A method of determining an adverse event within a patient having an implantable blood pump, the implantable blood pump comprising a motor and being configured to cause blood flow in the patient, the method comprising:

controlling, by processing circuitry, the implantable blood pump to operate the motor;

determining, by the processing circuitry, a first plurality of power consumption trends of the implantable blood pump, while the motor is operating, using a first low-pass filter;

determining a second plurality of power consumption trends of the implantable blood pump, while the motor is operating, using a second low-pass filter;

determining a plurality of power trend differences between the plurality of power consumption trends, wherein each power trend difference of the plurality of power trend differences comprises a difference between a value of the first plurality of power consumption trends and a corresponding value of the second plurality of power consumption trends, wherein the value of the first plurality of power consumption trends is determined based on a first filter interval and the corresponding value of the second plurality of power consumption trends is determined based on a second filter interval that is greater in duration than the first filter interval;

determining an accumulation value based on an accumulation of the power trend differences during a time interval using an integrator; and generating an alarm in response to the accumulation value exceeding a pre-determined threshold, wherein the alarm indicates an adverse event associated with the implantable blood pump in the patient, the adverse event including one of a presence of thrombus, an occlusion in the patient, a gastrointestinal bleed in the patient, or an ingestion.

14. The method of claim 13, wherein determining the first plurality of power consumption trends of the implantable blood pump using the first low-pass filter comprises determining a short-term trend using the first low-pass filter; and determining the second plurality of power consumption trends of the implantable blood pump using the second low-pass filter comprises determining a long-term trend using the second low-pass filter.

15. The method of claim 13, wherein the first low-pass filter comprises a first moving average filter defining a first moving average and the second low-pass filter comprises a second moving average filter defining a second moving average, wherein the second moving average is longer than the first moving average.

16. The method of claim 13, wherein the second low-pass filter has a cutoff frequency lower than a cutoff frequency of the first low-pass filter.

17. The method of claim 13, further comprising:

determining the pre-determined threshold using a percentage of at least one power consumption trend of the second plurality of power consumption trends.

18. The method of claim 13, further comprising:

determining an expected power of the implantable blood pump for a selected speed of the implantable blood pump;

determining a speed-dependent threshold using the expected power;

determining a real-time pump power for the implantable blood pump at the selected speed; comparing the speed-dependent threshold to the real-time pump power; and generating a second alarm in response to the real-time pump power exceeding the speed-dependent threshold.

* * * * *